US008934957B2

(12) United States Patent
Dias et al.

(10) Patent No.: US 8,934,957 B2
(45) Date of Patent: Jan. 13, 2015

(54) CONTACT SENSORS

(76) Inventors: Tilak Kithsiri Dias, Stockport (GB);
Paul Charles William Beatty, Stockport (GB); William Hurley, Stockport (GB);
Kimberley Mitcham, Leicester (GB);
Adrian Keith Griffiths, Cheshire (GB);
Rajcoomar Baboo Ramgulam, Manchester (GB)

( * ) Notice: Subject to any disclaimer, the term of this patent is extended or adjusted under 35 U.S.C. 154(b) by 1282 days.

(21) Appl. No.: 12/088,383

(22) PCT Filed: Sep. 29, 2006

(86) PCT No.: PCT/GB2006/003637
§ 371 (c)(1),
(2), (4) Date: Oct. 29, 2008

(87) PCT Pub. No.: WO2007/036741
PCT Pub. Date: Apr. 5, 2007

(65) Prior Publication Data
US 2009/0203984 A1 Aug. 13, 2009

(30) Foreign Application Priority Data
Sep. 29, 2005 (GB) .................................. 0519836.1

(51) Int. Cl.
*A61B 5/04* (2006.01)
*D04B 1/14* (2006.01)
(Continued)

(52) U.S. Cl.
CPC .............. *D04B 1/14* (2013.01); *A41D 13/1281* (2013.01); *A61B 5/0408* (2013.01); *A61B 5/6804* (2013.01); *D04B 1/18* (2013.01); *A61B 2562/164* (2013.01)
USPC ............................ 600/388; 300/396; 300/382

(58) Field of Classification Search
CPC .. A61B 5/0408; A61B 5/0531; A61B 5/0533; A61B 5/445; A61B 5/6801; A61B 5/6802; A61B 5/6804; A61B 5/6843; A61B 2560/0468; A61B 2562/0209; A61B 2562/0214; A61B 2562/125; A61B 2562/164

USPC .............. 442/117, 9, 111; 600/372, 382, 396, 600/395, 509, 388–390; 139/408–415, 423
See application file for complete search history.

(56) References Cited

U.S. PATENT DOCUMENTS 3,534,727 A * 10/1970 Roman .......................... 600/389
3,954,100 A 5/1976 Sem-Jacobsen
(Continued)

FOREIGN PATENT DOCUMENTS

EP 0 262 976 A2 4/1988
GB 2 143 135 A 2/1985
(Continued)

OTHER PUBLICATIONS

Patent Search Report for UK Application No. GB0519836.1 mailed Dec. 15, 2005.
(Continued)

*Primary Examiner* — Lee S Cohen
*Assistant Examiner* — Erin M Cardinal
(74) *Attorney, Agent, or Firm* — Adam W. Bell; Matthew R. Kaser

(57) ABSTRACT

A non-invasive sensor has a contact membrane (6,16) and a cover membrane (2,12), the cover membrane being adapted for extension of a body surface to project the contact membrane against a body surface beneath it. The contact membrane will normally be attached to the cover membrane around its periphery such that at least one of the membranes forms a convex outer surface, and a spacing material (8,20) can be interposed between the membranes to achieve this object. The cover membrane may extend over a support element (10), with the contact membrane overlaying and spaced from the other face of the support element by spacing material.

28 Claims, 2 Drawing Sheets

(51) Int. Cl.
  *A41D 13/12* (2006.01)
  *A61B 5/0408* (2006.01)
  *A61B 5/00* (2006.01)
  *D04B 1/18* (2006.01)

(56) References Cited

U.S. PATENT DOCUMENTS

| | | | | |
|---|---|---|---|---|
| 4,016,868 A * | 4/1977 | Allison | | 600/388 |
| 4,300,575 A | 11/1981 | Wilson | | |
| 4,580,572 A * | 4/1986 | Granek et al. | | 600/388 |
| 4,679,563 A * | 7/1987 | Wada et al. | | 600/391 |
| 4,715,235 A * | 12/1987 | Fukui et al. | | 73/862.68 |
| 4,729,377 A * | 3/1988 | Granek et al. | | 600/393 |
| 4,919,148 A * | 4/1990 | Muccio | | 607/152 |
| 5,218,973 A | 6/1993 | Weaver et al. | | |
| 5,263,481 A * | 11/1993 | Axelgaard | | 600/392 |
| 5,336,255 A * | 8/1994 | Kanare et al. | | 607/149 |
| 6,047,203 A | 4/2000 | Sackner et al. | | |
| 7,240,522 B2 * | 7/2007 | Kondou et al. | | 66/195 |
| 7,319,895 B2 * | 1/2008 | Klefstad-Sillonville et al. | | 600/388 |
| 2004/0260167 A1 * | 12/2004 | Leonhardt et al. | | 600/390 |
| 2005/0059896 A1 * | 3/2005 | Drakulic | | 600/509 |
| 2006/0135863 A1 * | 6/2006 | Birnbaum et al. | | 600/388 |
| 2006/0211934 A1 * | 9/2006 | Hassonjee et al. | | 600/372 |
| 2007/0038057 A1 * | 2/2007 | Nam et al. | | 600/388 |
| 2007/0073131 A1 * | 3/2007 | Ryu et al. | | 600/388 |
| 2007/0083096 A1 * | 4/2007 | Paradiso | | 600/388 |
| 2007/0089800 A1 * | 4/2007 | Sharma | | 139/388 |
| 2008/0114232 A1 * | 5/2008 | Gazit | | 600/390 |
| 2009/0018428 A1 * | 1/2009 | Dias et al. | | 600/388 |
| 2009/0227856 A1 * | 9/2009 | Russell et al. | | 600/388 |
| 2010/0324405 A1 * | 12/2010 | Niemi et al. | | 600/396 |

FOREIGN PATENT DOCUMENTS

| | | |
|---|---|---|
| GB | 2143135 A | 2/1985 |
| WO | 01/02052 A2 | 1/2001 |
| WO | 02/40091 A2 | 5/2002 |
| WO | WO-03/051456 A1 | 6/2003 |
| WO | 03/094717 A1 | 11/2003 |
| WO | WO-2005/053532 A1 | 6/2005 |
| WO | 2006/060934 A1 | 6/2006 |

OTHER PUBLICATIONS

International Search Report, PCT/GB2006/003637, mailed Dec. 19, 2006.

* cited by examiner

CONTACT SENSORS

CROSS-REFERENCE TO RELATED APPLICATIONS

This Application is a U.S. National Stage filing under §371 of International Application No. PCT/GB2006/003637, with an international filing date of 29 Sep. 2006, now pending, claiming priority from Great Britain Application No. GB 0519836.1, with a filing date of 29 Sep. 2005, now pending, and herein incorporated by reference.

TECHNICAL FIELD

This invention relates to contact sensors from monitoring activity at a body surface. Particularly, it relates to non-invasive sensors for attachment to or location on a body surface, for monitoring physiological signals. Such sensors can be incorporated in garments, as described in a paper presented to the Medicom 2004 conference by R. Paradiso, G. Loriga and N. Taccini, entitled, "Wearable Health Care System For Vital Signs Monitoring". Reference is also directed to published Patent Specification No. WO04/100784, incorporated herein by reference, disclosing knitted transducers which may serve as such sensors.

The sensors disclosed herein can also be used with the knitting techniques disclosed in our co-pending International Application also filed on 29 Sep. 2006 with priority from British Application No: GB05/19837.9, incorporated by reference, and in garments and other knitted products made using those techniques.

BACKGROUND OF THE INVENTION

Non-invasive sensors for monitoring activity at a body surface need to make intimate contact with the surface in order to function effectively. Such contact has been previously assured by adhering the sensor to the skin surface, or at least interposing a layer of conductive jelly to ensure the transmission of signals from the body to the sensor. These techniques have been felt to be somewhat clumsy and can create discomfort. Some research has therefore been directed at the attachment or incorporation of sensors on garments, with a respective garment holding the sensor in place.

SUMMARY OF THE INVENTION

According to the present invention, a non-invasive sensor monitoring activity at a body surface comprises a contact membrane and an adjacent cover membrane. The contact membrane is attached to the cover membrane around it's periphery such that at least one of the membranes forms a convex outer surface. The cover membrane is adapted to be extended over the body surface to project the contact membrane against the body surface beneath it. Preferably, the cover membrane is more elastic than the contact membrane, such that the contact membrane is elastically unstretched when the cover membrane is extended over the body surface.

A sensor according to the invention may be reinforced by a support element. In this variant, the sensor comprises a cover membrane extending over one face of the element, which may be planar or curved; a contact membrane overlaying the other face of the support element and spaced from the support element by a spacing material, the contact membrane being substantially inextensible and attached to the cover membrane at the periphery of the support element. The cover membrane is normally stretched over the one face of the support element, and the support element may be held securely to the cover membrane by elastic sections. Such elastic sections will normally be more elastic than the cover membrane and may be fabric sections comprising low power elastomeric yarns. The cover membrane may also be a fabric, but comprising high power elastomeric yarns.

Sensors of the invention may be made part of a garment which delivers localised higher pressure to the body of the wearer at the sensor areas while delivering low, comfortable pressure to the rest of the body. In sensors that incorporate a support element as described above, the support element enables the contact member to preserve its shape and dimensions notwithstanding deformation or extension of the garment of which it is a part. Its shape will normally be convex, but in some circumstances the contact membrane can present a planar surface for contact with the body surface.

The contact membrane will normally be attached to the cover membrane substantially continuously around its periphery, and the space between the membrane may be occupied by a filler material. If the attachment is continuous around the contact membrane periphery, and the materials of the respective membranes are impermeable, such a filler material may be liquid or at least a semi-solid. However, a dry filler material is normally preferred.

In sensors of the invention, the contact membrane may have transmissible characteristics which vary on distortion, enabling movement of the body surface to be monitored directly. Such sensors are described in the International patent publication referred to above. Alternatively, the contact membrane can form an electrode for receiving and transmitting electronic signals. It may comprise a knitted structure. Typically, such an electrode is a multi-point electrode, and the multi-points preferably comprise particles of silver or silver chloride at the surface of the membrane. Silver or silver chloride is preferred for the reason that the electrical conductance required to ensure good transmission of electrical signals is much less using these materials than other available options. Some experimental work has shown that electrodes knitted with silver yarns provided good quality ECG signals with a contact pressure around 10 Hgmm compared to stainless steel which required a minimum of 100 Hgmm pressure to achieve a similar signal quality. Lower contact pressures will of course be more comfortable to the wearer.

The requisite contact pressure can be provided in an elastomeric knitted structure created by "knitting-in" a covered elastomeric yarn or a conventional yarn blended with an elastomeric yarn such as Lycra. Such an elastomeric knitted structure, which may be the basic structure of a health monitoring vest, would form the cover membrane.

As described above, one of the membranes in sensors of the invention will normally form a convex outer surface. When the cover membrane is extended over a body surface, this will ensure that the contact membrane is urged against the surface for the monitoring of physiological signals. This can be accomplished by the manner in which two membranes of different elastic modulus are attached to each other. A substantially similar effect can be achieved in a single knitted fabric having a contact side and a cover side, by increasing the stitch density on the contact side relative to the cover side over an area thereof which forms a convex surface on the contact side. The knitted fabric can then be extended over a body surface in the same way as described above, to project the area of increased stitch density against the body surface beneath it.

When a sensor according to the invention is to be attached to or incorporated in a garment, electrical connections to and from the sensor can comprise conductive yarns in the garment. Where the sensor itself comprises a knitted element, conductive yarns can be used to form the sensor. Particularly in the embodiment just referred to in which the sensor comprises a knitted fabric having a contact side and a cover side, the area of increased stitched density can comprise conductive yarns.

BRIEF DESCRIPTION OF THE DRAWINGS

The invention will now be described by way of example and with reference to the accompanying schematic drawings wherein.

DETAILED DESCRIPTION OF THE INVENTION

Figure 1:
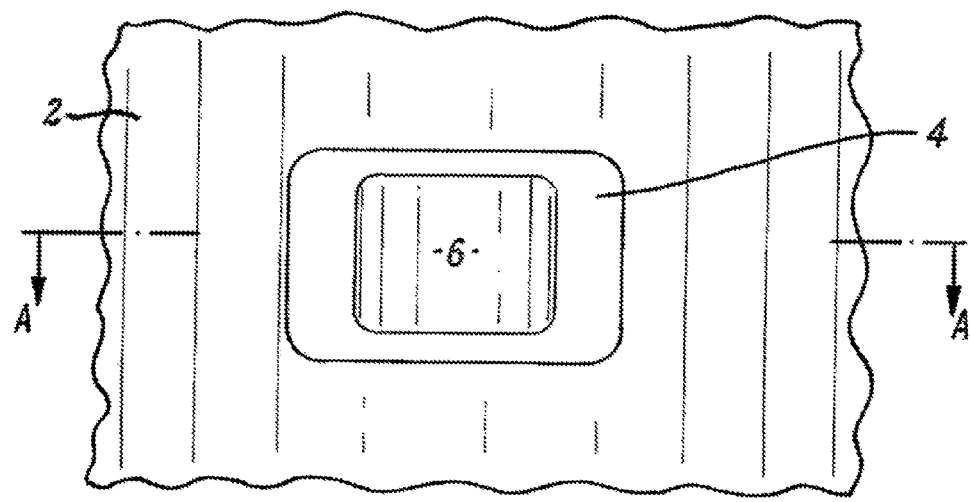
FIG. 1 shows a plan view of a sensor according to one embodiment of the invention.
Figure 2:
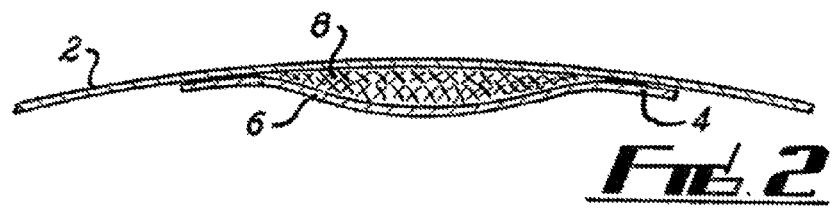
FIG. 2 shows a cross section taken on line A-A of FIG. 1.

The sensor shown in FIGS. 1 and 2 comprises a cover membrane 2 and a contact membrane 4 attached thereto. In a central section 6 of the contact membrane, it is spaced from the cover membrane 2 to form a space 8, and a convex outer surface, as shown in FIG. 2. The space 8 may be occupied by a filler material to maintain the separation between the membranes in this section. If the respective membranes are impermeable, and the attachment between them around the section 6 is also sealed, then the filler material may be liquid, although a dry material is preferred. Of course, if the space 8 is effectively sealed, air confined therein can be sufficient to form a bubble if specific application of pressure is acquired. In many applications however, providing a convex outer surface is formed, then when the cover membrane is extended the contact membrane will be sufficiently urged against a respective body surface.

The sensor illustrated in FIGS. 1 and 2 would normally comprise an electrode, for receiving and transmitting electronic signals representative of physiological activity. A preferred form of electrode is a multi-point electrode, and a preferred multi-point electrode, will comprise a continuous layer of silver on the electrode surface and silver chloride particles at the electrode surface. If the contact membrane is a fabric, then a multipoint electrode may be created from a silver yarn or with a yarn with a continuous layer of silver on its surface. Such a contact membrane can be a knitted layer comprising electrically conductive yarns; for example, yarns comprising silver, gold or platinum. With such yarns, a knitted fabric can create multiple contact points at the yarn cross over points of stitches. Silver chloride particles can be conveniently located within the surface of the knitted electrode. Conductive yarns in the fabric may be used to carry electronic signals between the particles and remote terminals. In the case of knitted electrodes the conductive yarns will be connected to the electrodes during the knitting process.

Figure 3:
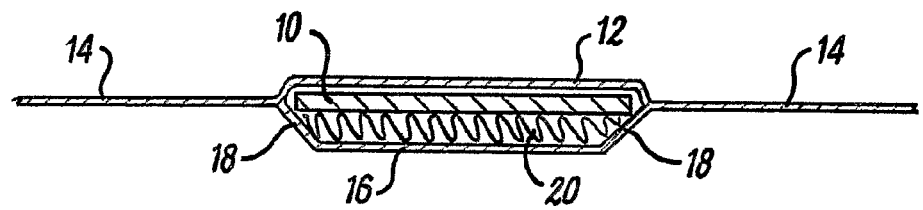
FIG. 3 is a cross-section similar to that of FIG. 2 of another embodiment of the invention.

FIG. 3 shows a cross-section through a sensor according to a variant of the invention which is reinforced by a support element 10. The cover membrane 12 extends over and is preferably stretched over the support element 10 to opposite sides of the support element. At this point, the cover membrane 12 can merge with or even be part of contiguous sections 14 for attachment to or incorporation into a garment. The support element 10 and the cover membrane 12 effectively define fixed boundaries, relative to which the contact membrane 16 is located.

The cover membrane 12 is typically a stretchable fabric such as a knitted fabric, and as noted above can be stretched over the support element 10. It can be attached directly to the support element 10, but is normally attached indirectly by connection to the contact membrane. The contact membrane 16 is either inextensible, or relatively inextensible relative to the cover membrane. In the embodiment illustrated, it is attached to the cover membrane either directly or indirectly, by elastic sections 18 on either side or disposed around the contact membrane 16. The elastic sections will normally be high stretch sections, typically comprising low power elastomeric yarns. The support element 10 and the contact membrane 16 will normally be square or rectangular, with well defined straight edges, suitably oriented relative to the plane or preferred axis or axes of stretch of the garment fabric 14. However, other shapes may be used for the support element and contact membrane and if the shape chosen is circular of course, a single elastic section 18 can circumscribe the contact element 16.

The contact element 16 is preferably spaced from the support element 10 by a filler or packing material 20. This can be selected to give the outer face of the contact membrane a desired profile, which may be convex or flat depending on the intended use of the sensor. The cross-sectional area of the contact membrane 16 is normally less than that of the support element 10 to orient the elastic sections 18 as indicated, such that they make an acute angle with the support element 10.

Figure 4:
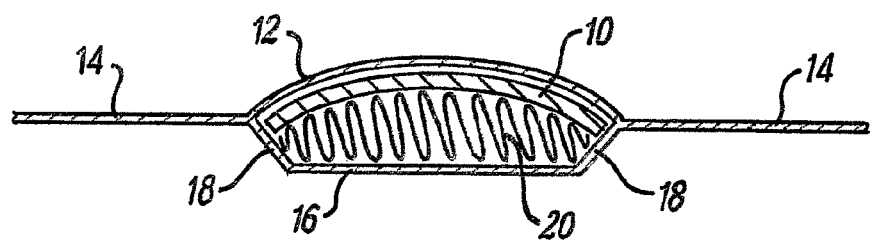
FIG. 4 shows a variation of the embodiment of FIG. 3.

In the embodiment illustrated in FIG. 3, the support element 10 is shown as being generally planar. There can though, be circumstances in which a curved shape would be desirable. Such a variation is illustrated in FIG. 4. The purpose of this variation is to generate increased pressure between the contact membrane 16 and the body surface to which it is applied. When the cover membrane 10 is stretched over the support element, it generates forces on the support element urging the contact membrane against the respective body surface. In other respects, the construction of this embodiment is similar to that of FIG. 3. The sensor of FIGS. 3 and 4, as with that of FIGS. 1 and 2, will typically comprise an electrode with the sensing contacts being formed on the contact membrane as described above.

Figure 5:
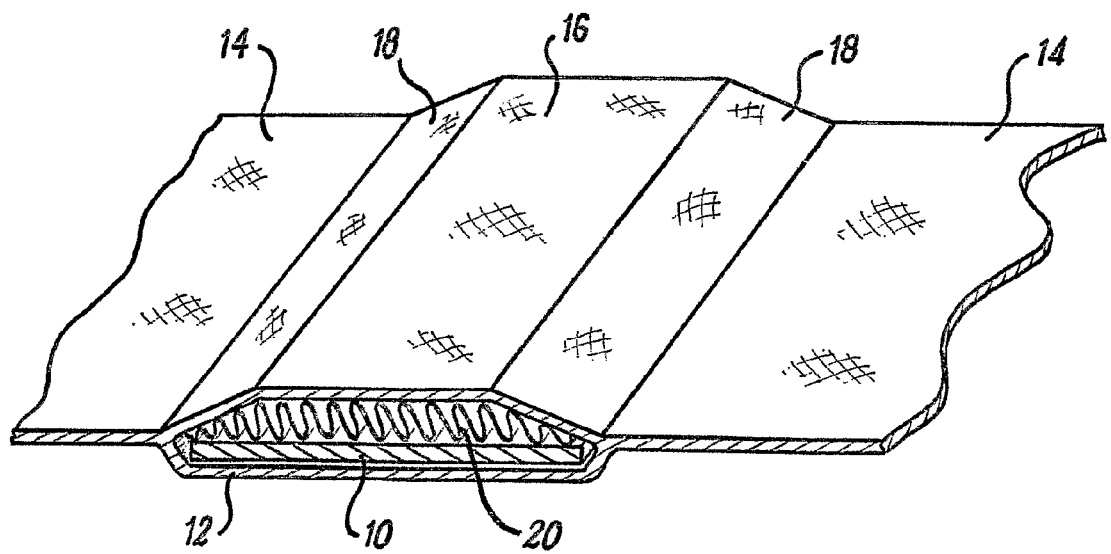
FIG. 5 is a perspective view of a sensor similar to that shown in FIG. 3.

The formation of a sensor of the type shown in FIG. 3, on a flat bed knitting machine, is described with reference to FIG. 5. A relatively high modulus elastic yarn is knitted to create the cover membrane 12, as an extension of adjacent garment sections 14. This is knitted in a tube, first on the front needle bed and then across the rear needle bed of the knitting machine. By doing so with the same feeder, both sides are connected. The relative high modulus elastic yarn is then knitted only on the front needle bed while the conductive yarn is knitted on the rear bed to form the contact membrane 16. Four courses of the low modulus elastic yarn are knitted on the rear needle bed to form the elastic sections 18, connecting the high modulus yarns of the cover membrane 12 and the conductive yarns of the contact membrane 16. As shown, the contact and cover membranes form an open-ended enclosure in which the packing material 20 can be easily secured by attachment to one or other of the membranes 12, 16. The ends may though be closed if desired, by additional elastic sections (18) or ties (not shown).

For the cover membrane, and for the adjacent garment sections, a suitable high modulus elastic yarn has a core of 570 DT Lycra T902C (64.0%) with outer and inner covers (each 18.9%) of 33/10 text nylon 66. A suitable relatively low modulus yarn for the elastic sections is based on a core of 44f34 Nylon/78's Lycra (33.1%) with inner and outer covers of 1/78f46 textured nylon PA66DD (33.3% and 33.6% respectively).

Figure 6:
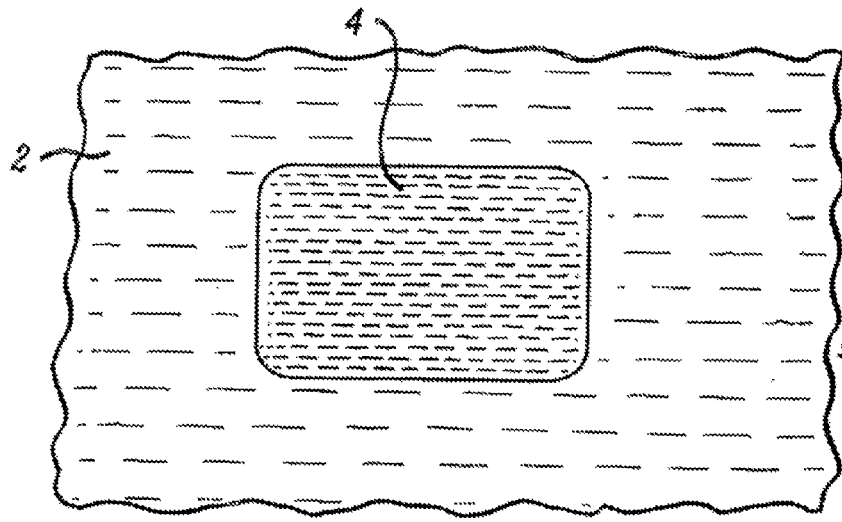
FIG. 6 is a view similar to that of FIG. 1 of a fabric sensor embodying the invention.

FIG. 6 illustrates an embodiment of the invention in which both the cover membrane and the contact membrane is a fabric. Knitted fabrics will normally be used, but in some circumstances woven or stitched-bonded fabrics can also be effective. If prepared quite separately, then the contact membrane can be attached to the cover membrane precisely round its periphery, such that the contact membrane defines the entire sensor section. It will be appreciated that conductive yarns may be incorporated in the structure of the cover membrane fabric to carry electronic signals to and from the contact membrane, which may also comprise conductive yarns. As discussed above, this can facilitate the formation of a multi-point electrode at the contact membrane surface.

Figure 7:
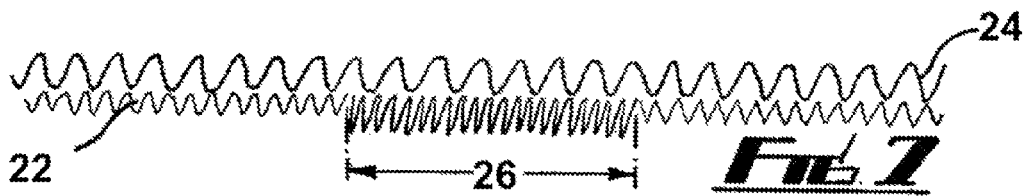
FIG. 7 is a cross section through a single layer of fabric embodying the invention.

FIG. 7 shows a cross section through a single layer fabric having a contact side 22 and a cover side 24, but in which a convex surface is created on the cover side by an area 26 of increased stitch density on the contact side. While not comprising separately definable membranes, a similar effect is achieved when the fabric is extended over a body surface. Because of the increased density in the area, the contact surface in this area 26 will be urged against the body surface there beneath. The area can therefore be used as a sensor in the same way as the contact membranes described above with reference to FIGS. 1 to 5.

The invention claimed is:

1. A non-invasive sensor for monitoring activity at a body surface, comprising a contact membrane; a cover membrane, the cover membrane having a greater elasticity than the contact membrane, and a support element between the contact membrane and the cover membrane and over which the cover membrane is stretched, the contact membrane being attached to the cover membrane at the periphery of the support element such that at least one of the membranes forms a convex outer surface, the cover membrane being adapted for extension over a body surface to project the contact membrane against a body surface beneath it, wherein the contact membrane is attached to the cover membrane by additional elastic sections.

2. A sensor according to claim 1 wherein the additional elastic sections comprise elastomeric yarns.

3. A sensor according to claim 1 wherein the additional elastic sections are knitted.

4. A sensor according to claim 1 wherein at least one of the contact membrane or the cover membrane are knitted.

5. A sensor according to claim 4 wherein the cover membrane is a knitted fabric comprising elastomeric yarns.

6. A sensor according to claim 1 wherein the contact membrane is attached to the cover membrane substantially continuously around its periphery.

7. A sensor according to claim 1 wherein a space between the contact membrane and the cover membrane is occupied by a filler material.

8. A sensor according to claim 1 wherein the contact membrane forms an electrode.

9. A sensor according to claim 8 wherein the electrode is a multi-point electrode.

10. A sensor according to claim 9 wherein the multi-points comprise particles of silver chloride at a surface of the membrane.

11. A sensor according to claim 9 wherein the contact membrane is a textile structure comprising electrically conductive yarns.

12. A sensor according to claim 8 wherein the contact membrane is a knitted layer comprising electrically conductive yarns.

13. A sensor according to claim 12 wherein the contact membrane comprises multiple contact points at the yarn cross over points of stitches.

14. A sensor according to claim 12 wherein the conductive yarns comprise one of silver, gold or platinum.

15. A material incorporating a sensor according to claim 1.

16. A material according to claim 15 including at least one conductor extending from the sensor to an edge of the material.

17. A knitted material according to claim 15.

18. A garment comprising a material according claim 15.

19. A non-invasive sensor comprising a cover membrane extending over one face of a support element; a contact membrane overlaying another face of the support element and spaced from the support element by a spacing material, the contact membrane being substantially inextensible and attached to the cover membrane at the periphery of the support element by elastic sections and the cover membrane being stretched over the support element; wherein the contact membrane forms an electrode; or wherein at least one of the cover and contact membranes are knitted.

20. A non-invasive sensor according to claim 19 wherein the support element is planar.

21. A non-invasive sensor according to claim 19 wherein the support element is curved with its one face being convex.

22. A sensor according to claim 19 wherein the elastic sections are fabric comprising elastomeric yarns.

23. A sensor according to claim 19 wherein the contact membrane is attached to the cover membrane substantially continuously around its periphery.

24. A sensor according to claim 19 wherein a space between the contact membrane and the cover membrane is occupied by a filler material.

25. A sensor according to claim 19 wherein the contact membrane is a textile structure having conductive yarns.

26. A material incorporating a sensor according to claim 19.

27. A method of monitoring physical movements of a body surface comprising attaching to the body a non-invasive sensor for monitoring activity at the body surface, comprising a contact membrane, a cover membrane, the cover membrane having a greater elasticity than the contact membrane, and a support element between the cover membrane and the contact membrane over which the cover membrane is stretched, the contact membrane being attached to the cover membrane at the periphery of the support element the cover membrane projecting the contact membrane against a body surface beneath it, wherein the contact membrane is attached to the cover membrane by additional elastic sections, and monitoring deformation of the sensor in response to movements of the body surface.

28. A method according to claim 27 wherein the body surface is a human body surface, and the sensor is part of a garment on the human body.

* * * * *